(12) United States Patent
Sarvestani et al.

(10) Patent No.: US 9,248,000 B2
(45) Date of Patent: Feb. 2, 2016

(54) SYSTEM FOR AND METHOD OF VISUALIZING AN INTERIOR OF BODY

(75) Inventors: Amir Sarvestani, Freiburg (DE); Hans Schoepp, Freiburg (DE); Klaus Welte, Freiburg (DE)

(73) Assignee: STRYKER EUROPEAN HOLDINGS I, LLC, Kalamazoo, MI (US)

( * ) Notice: Subject to any disclaimer, the term of this patent is extended or adjusted under 35 U.S.C. 154(b) by 1681 days.

(21) Appl. No.: 12/583,148

(22) Filed: Aug. 14, 2009

(65) Prior Publication Data

US 2010/0039506 A1 Feb. 18, 2010

(51) Int. Cl.
*A62B 1/04* (2006.01)
*A61B 19/00* (2006.01)

(52) U.S. Cl.
CPC ......... *A61B 19/5244* (2013.01); *A61B 19/5212* (2013.01); *A61B 2019/5229* (2013.01); *A61B 2019/5255* (2013.01); *A61B 2019/5291* (2013.01); *A61B 2019/5437* (2013.01); *A61B 2019/5483* (2013.01); *A61B 2019/5495* (2013.01)

(58) Field of Classification Search
CPC ... H04N 2005/2255; H04N 7/183; A61B 1/05
USPC .................. 348/65, 73, 75, 76, 77
See application file for complete search history.

(56) References Cited

U.S. PATENT DOCUMENTS

| 5,694,142 | A | 12/1997 | Dumoulin et al. |
|---|---|---|---|
| 5,704,897 | A | 1/1998 | Truppe |
| 5,792,147 | A | 8/1998 | Evans et al. |
| 5,795,294 | A | 8/1998 | Luber et al. |
| 5,848,967 | A | 12/1998 | Cosman |
| 6,246,900 | B1 | 6/2001 | Cosman et al. |
| 6,978,167 | B2 | 12/2005 | Dekel et al. |

(Continued)

FOREIGN PATENT DOCUMENTS

| DE | 695 03 814 | 12/1998 |
|---|---|---|
| DE | 102 38 011 | 3/2004 |

(Continued)

OTHER PUBLICATIONS

European Search Report dated Nov. 27, 2009, Application Patent No. 09010523.0-1269.

(Continued)

*Primary Examiner* — Philip Chea
*Assistant Examiner* — Van Kim T Nguyen
(74) *Attorney, Agent, or Firm* — Howard & Howard Attorneys PLLC (57) ABSTRACT

A navigation system includes a display monitor, a CPU, and a camera, wherein the camera is mounted to a back side of the display monitor to form a monitor unit. One or more reference units are placed on a body while acquiring an image data set, and are tracked during a surgical operation by the monitor unit to register and correlate a position of a visual image of an exterior surface of the body with the image data set including information concerning internal structures of the body. The image data set is displayed on the display monitor superimposed in registration over the visible image of the exterior of the body with an angle of view and aperture in accordance with the actual position of the camera, whereby the display monitor displays the internal structures corresponding to the line-of-sight of the camera and the observer.

25 Claims, 9 Drawing Sheets

(56) References Cited

U.S. PATENT DOCUMENTS

| | | | |
|---|---|---|---|
| 7,231,063 | B2 | 6/2007 | Naimark et al. |
| RE43,328 | E * | 4/2012 | Foley et al. .................... 600/429 |
| 2002/0087075 | A1* | 7/2002 | Bucholz ......................... 600/429 |
| 2002/0087101 | A1* | 7/2002 | Barrick et al. ................. 600/587 |
| 2002/0173783 | A1* | 11/2002 | Ohno et al. ...................... 606/10 |
| 2003/0130576 | A1* | 7/2003 | Seeley et al. .................. 600/426 |
| 2004/0082854 | A1* | 4/2004 | Essenreiter et al. ........... 600/429 |
| 2005/0015005 | A1* | 1/2005 | Kockro .......................... 600/427 |
| 2005/0171558 | A1* | 8/2005 | Abovitz et al. ................ 606/130 |
| 2005/0180919 | A1* | 8/2005 | Tedeschi ........................ 424/9.4 |
| 2005/0273004 | A1* | 12/2005 | Simon et al. ................... 600/424 |
| 2006/0176242 | A1 | 8/2006 | Jaramaz et al. |
| 2007/0018975 | A1 | 1/2007 | Chuanggui et al. |
| 2007/0019936 | A1* | 1/2007 | Birkenbach et al. ............. 396/14 |
| 2007/0144026 | A1* | 6/2007 | Mitchell et al. ................. 33/707 |
| 2007/0238981 | A1 | 10/2007 | Zhu et al. |
| 2008/0208041 | A1 | 8/2008 | Gilboa |
| 2008/0306490 | A1* | 12/2008 | Lakin et al. ................... 606/130 |
| 2010/0017178 | A1* | 1/2010 | Tsuk et al. ......................... 703/6 |

FOREIGN PATENT DOCUMENTS

| | | |
|---|---|---|
| DE | 10 2005 058 2 | 6/2007 |
| EP | 1470791 | 10/2004 |
| WO | WO99/38449 | 8/1999 |
| WO | WO2004/075768 | 10/2004 |
| WO | WO 2005/091220 | 9/2005 |
| WO | WO 2007/065750 | 6/2007 |
| WO | WO 2008/036050 | 3/2008 |

OTHER PUBLICATIONS

EPO Extended Search Report dated Feb. 15, 2010, Application Patent No. 09010523.0-1269/2153794.

"Stereoscopic Augmented Reality System for Computer Assisted Surgery", Liévin et al., CARS 2001, Berlin, Germany, Jun. 27-30, 2001, 5 pages.

"Intuitive and Lightweight User Interaction for Medical Augmented Reality", Fischer et al., VMV 2005, Erlangen, Germany, Nov. 16-18, 2005, 9 pages.

"Augmented Reality in Surgery", James C. Thomas, Studentbmj, vol. 16, Mar. 2008, pp. 108-109.

"Augmented Reality in Surgical Procedures", Samset et al., Proceedings of SPIE 2008;6806, 12 pages.

"ActiSight. Precisely What You've Been Waiting for", ActiViews, Inc., 2008, 2 pages.

* cited by examiner

SYSTEM FOR AND METHOD OF VISUALIZING AN INTERIOR OF BODY

CROSS REFERENCE TO RELATED APPLICATIONS

This application claims the benefit of Provisional U.S. Patent Application No. 61/189,300, filed Aug. 15, 2008, which is incorporated by reference in its entirety herein.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Invention

The present invention relates to a method and/or system of navigation inside an enclosed space or in a space not readily viewable to an operator.

2. Description of the Background of the Invention

State-of-the art imaging devices have been developed to capture pre-operative and intra-operative images that are used in planning and execution of diagnostic and therapeutic medical procedures. However, some such imaging devices expose patients and operating room staff to intensive radiation or magnetic fields and do not typically allow correlation of images with a patient. Surgical navigation systems have also been developed that allow correlation of images with a patient but add cost and complexity to the procedure. Moreover, known surgical navigation systems do not satisfactorily solve the problem of hand-eye coordination, as the view of the images on a display monitor is not correlated with the spatial position of the patient. To overcome the hand-eye coordination problem, head-mounted displays are available, but require a user, such as a surgeon, to wear a head-mounted fixture.

In one example, tracked display monitors in conjunction with surgical navigation systems are available to correlate images with the spatial position of a patient. However, to locate the display monitor and correlate displayed images with a patient, a tracking system to sense the position of the display monitor and the patient is needed, e.g., an infrared tracking or electromagnetic tracking system. Such systems need a separate tracking device for the display monitor and may suffer from line-of-sight issues or field distortion issues. Moreover, such systems add complexity and cost to the overall procedure.

In another example, a system that utilizes a tracked display monitor generally requires a display monitor, a monitor tracker, a video camera, a video camera tracker, and a navigation camera in order to correlate images with the spatial position of a patient. In addition, special efforts are required to keep the video camera tracker, the monitor tracker, the patient tracker, and eventually a tool tracker, simultaneously within the view of the navigation camera. In addition, such a surgical navigation system is not adapted to align the viewing direction of the video camera with the viewing direction of a surgeon.

SUMMARY OF THE INVENTION

According to one aspect of the invention, a system for visualizing an interior of a body from an exterior position includes a navigation system having a monitor and a camera, wherein the camera is fixed to the monitor and serves as a reference system, and wherein the monitor is movably positionable between an operator and the body. The system further includes an optical reference unit adapted to be attached to the body for tracking movements of the body, an electronic processing device in communication with the navigation system, and an image data set including features of the interior of the body, the image data set being accessible to the processing device. The processing device receives an optical image of an exterior surface of the body obtained with the camera, registers the image data set with respect to the reference system by correlating a position of the optical reference unit in the image data set with a position of the optical reference unit in the optical image, and causes the monitor to display the image data set superimposed and in registration with the optical image in a position and orientation that represents an angle of viewing and an aperture angle of the camera relative to the body.

According to another aspect of the invention, an optical reference unit for use with an optical surgical navigation system. The optical reference unit includes a substrate, an optical pattern on the substrate, and a marker carried by the substrate. The marker is visible in a pre-operative image, the optical pattern is visible to a video camera, and the marker is in a unique identifiable position in relation to the optical pattern, whereby the location of the marker can be uniquely registered to the optical pattern at each of a plurality of viewing angles.

According to a further aspect of the invention, a method of visualizing an interior of a body from an exterior viewing position includes the steps of obtaining an internal image data set of an internal portion of the body, wherein the internal image data set includes a reference location on an exterior surface of the body, and accessing the internal image data set with a navigation system comprising a visual display screen, a camera fixed to the visual display screen in alignment with the display screen, and a digital electronic processing unit in data communication with the camera and the display screen, wherein the camera serves as a reference system and the visual display screen is movably positionable between an operator and the body. The method further includes the steps of obtaining a visual image of an exterior of the body with the camera, wherein the reference location is visible in the visual image and oriented to the reference system, identifying the reference location in the visual image, and registering with the digital electronic processing unit the internal image data set to the visual image in relation to the reference system using the reference location. Further, the method includes the step of displaying the internal image data set superimposed and in registration with the visual image on the visual display screen in a position and orientation that represents an angle of view and an aperture angle of the camera and the visual display screen relative to the body.

According to yet another aspect of the invention a method of registering an image data set of a body with a visual image of an exterior surface of the body includes the steps of affixing at least one reference unit to the exterior surface of the body, wherein the reference unit has one or more features that create a unique image signal in the image data set and a unique representation in the visual image, and acquiring an image data set that includes the unique image signal of the reference unit. The method further includes the steps of identifying the position of the reference unit with respect to a coordinate system of the image data set, acquiring a visual image of an exterior surface of the body that includes the unique representation of the reference unit, identifying the position of the reference unit in the visual image, and matching the spatial position of the reference unit in the image data set with the spatial position of the reference unit in the visual image to automatically register the image data set with the visual image of the body.

According to a still further aspect of the invention, a computer-readable medium that carries a program executable by one or more digital electronic processing devices to visualize the interior of a body includes a first routine that receives an image data set of a body including a unique image signal of a reference unit affixed to a body, a second routine that identifies a position of the reference unit with respect to a coordinate system of the image data set, a third routine that receives a visual image of an exterior of the body including a visual representation of the reference unit, a fourth routine that identifies the position of the reference unit in the visual image, a fifth routine that matches the spatial position of the reference unit in the image data set with the spatial position of the reference unit in the visual image to automatically register the image data set with the visual image of the body, and a sixth routine that causes the image data set and the visual image of the body to be visually displayed on a display device with the image data set superimposed in registration with the visual image of the body.

Other aspects and advantages of the present invention will become apparent upon consideration of the following detailed description.

DETAILED DESCRIPTION

In some embodiments, a navigation system of the present disclosure includes a visual display monitor, a central processing unit ("CPU"), and a camera. The camera is rigidly mounted to a back side of the display monitor to form a monitor unit. The monitor unit has a data interface to import one or more image data sets that contain data relating to internal or sub-surface structures, such as pre-operative image data sets obtained through various modalities including 2-dimensional X-ray images, three-dimensional computed tomography ("CT") scans, magnetic resonance ("MR") images, positron emission tomography ("PET") images, and the like. In one example, at least one (and in some embodiments three or more) reference units are placed on a patient and identified by the monitor unit to register a visible image of the patient with an image data set. After the position of the patient and the image data set are registered, the image data set is displayed on the display monitor superimposed over the visible image of the patient. In another example, multiple reference units or a single reference unit that includes a unique optical pattern can be used to track the position of the patient in relation to the monitor unit and correlate the visible image and image data set with the actual position of the patient. In yet another example, the same one or more reference units are used to provide both registration and tracking functions.

Preferably, the pre-operative images are processed and displayed with an angle of view and aperture in accordance with the actual position of the monitor unit relative to the patient. When the monitor unit is positioned between an observer and the patient, the monitor unit displays a view of the internal structures of the patient from the image data that corresponds to the line-of-sight of the observer. Further, when the monitor unit is moved around the patient (or vice versa) the observer can view the internal structure of the patient from different directions and angles as if the observer were looking directly through the outer surface or skin of the patient through the camera. Still further, the rigid combination of the monitor and the camera in the monitor unit provides a global reference system that operates as a stand-alone navigation system that does not require additional tracking devices for the camera and/or monitor.

According to one aspect of the disclosure, a system for visualizing the interior of a body from an exterior position includes a navigation system having a monitor and a camera, a reference unit adapted to be attached to the body for tracking movements of the body, and a processing device. The camera is rigidly fixed to the monitor in order to serve as a reference system, and the monitor is movably positionable between an operator and the body. The processing device is configured to receive a visual image of at least a portion of an exterior surface of the body obtained with the camera, control the monitor to display the visual image, register an image data set with respect to the reference system of the navigation system by correlating points and/or a surface of the image data set with corresponding points and/or a corresponding surface on the visual image, and cause the monitor to display the image data superimposed with the visual image in a position and orientation that represents an angle of vision and an aperture angle of the camera relative to the body. The reference unit may include one or both of a tracking device functionality and a registration device functionality. In some embodiments, the reference unit may enable manual registration, and in other embodiments, the reference unit may enable automatic registration.

According to another aspect of the disclosure, a computer-readable medium that stores a program executable by one or more processing devices to visualize the interior of a body includes a first routine that receives an image data set including a unique image signal of a reference unit affixed to a body, a second routine that identifies a position of the reference unit with respect to a coordinate system of the image data set, a third routine that receives a visual image of an exterior of the body including a visual representation of the reference unit, a fourth routine that identifies the position of the reference unit in the visual image, and a fifth routine that matches the spatial position of the reference unit in the image data set with the spatial position of the reference unit in the visual image to automatically register the image data set with the visual image of the body, and sixth routine that causes the image data set and the visual image of the body to be visually displayed on a display device with the image data set superimposed in registration with the visual image of the body.

According to a further aspect of the disclosure, a method of visualizing an interior of a body from an exterior viewing position includes the steps of providing a navigation system including a monitor and a camera, wherein the camera is rigidly fixed to the monitor in order to serve as a reference system and the monitor is movably positionable between an operator and a body, tracking movements of the body, and obtaining a visual image of at least a portion of the body with the camera, wherein reference points are identified in the visual image, and displaying the visual image of at least a portion of the body on the monitor. The method further includes the steps of transferring an image data set of an internal portion of the body to the monitor, registering the image data set with respect to the reference system of the navigation system, and displaying the image data set on the monitor in a position and orientation that represents an angle of vision and an aperture angle of the camera relative to the body. The step of identifying a reference point may include the step of attaching a reference unit to the body. The step of registering may include performing a point by point correlation of reference points between the image data set and the visual image and/or the step of registering may include performing a surface to surface correlation between the image data set and the visual image. The method may further include the step of compensating for movements of the body with respect to the camera, which may further include the steps of tracking movements of the reference unit relative to the camera and modifying the displayed visual image and image data set to compensate for such movements. The method may further include the step of superimposing the displayed visual image and the image data set on the monitor. The method may also include the steps of defining additional virtual information with respect to the image data set and displaying selected additional information along with the image data set. The step of defining additional virtual information in some instances can include the steps of selecting one or more internal structures to display and defining a trajectory of an instrument to be inserted into the body. The step of registering may further include the steps of digitizing points on the body with a pointing device and correlating the digitized points with corresponding reference points of the image data set. The step of registering further may include the step selecting points and/or a surface of the image data set and corresponding points and/or a corresponding surface on the visual image with an input device, without the need for a pointing device. The method may further comprise the steps of tracking a surgical tool with known geometry that is equipped with at least one reference unit and superimposing a representation of the surgical tool on the monitor.

According to additional aspects of the disclosure, a method of registering an image data set of a body with a visual image of an exterior surface of the body includes the steps of affixing a reference unit to the body prior to the acquisition of an image data set of the body, wherein the reference unit is formed of a material and has a shape that creates a unique image signal in the image data set, acquiring an image data set that includes the unique image signal of the reference unit, and identifying the position of the reference unit with respect to a coordinate system of the image data set. The method further includes the steps of acquiring a visual image of an exterior surface of the body that includes a representation of the reference unit, and identifying the position of the reference unit in the visual image. Furthermore the method includes the step of matching the spatial position of the reference unit in the image data set with the spatial position of the reference unit in the visual image to automatically register the image data set with the visual image of the body. The method may further include the step of affixing at least three reference units to the body, the step of determining the orientation and size of the reference units based on a unique optical pattern disposed on each of the reference units, and the step of registering the position and orientation of the reference units with a coordinate system of the body. In some instances, a plurality of reference units is used to increase accuracy, field of view, and robustness of a navigation system, wherein the navigation system can include a monitor and a camera rigidly fixed to the monitor. The step of identifying the position of the reference unit in the visual image may include the step of identifying the center of the reference unit, and the step of matching may match the spatial position of the reference unit in the image data set with the center of the reference unit in the visual image.

Figure 1:
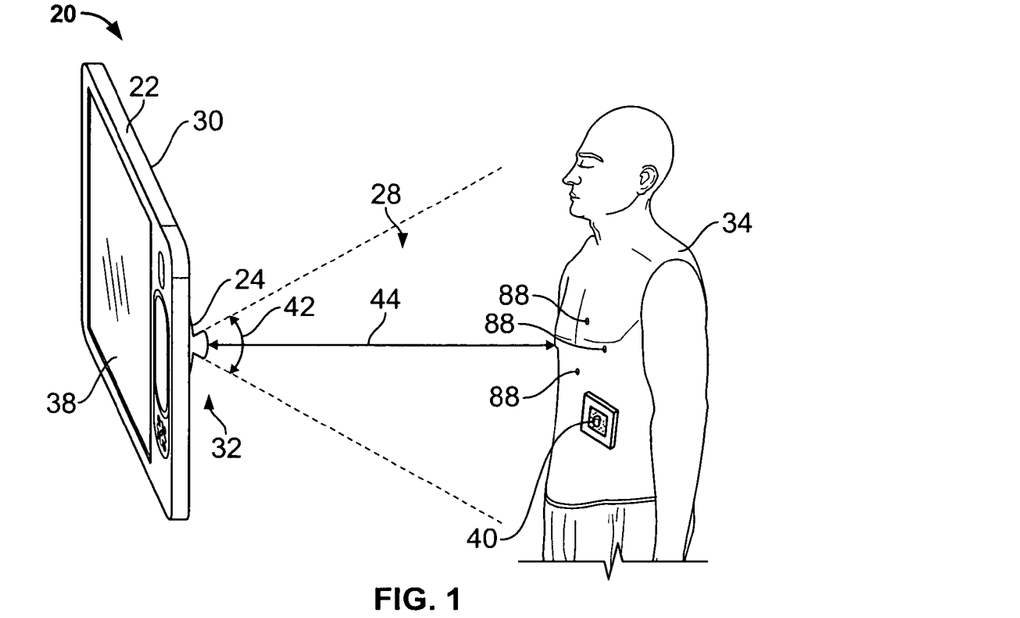
FIG. 1 shows a diagrammatic view of a navigation system with respect to a body of a patient.
Figure 2:
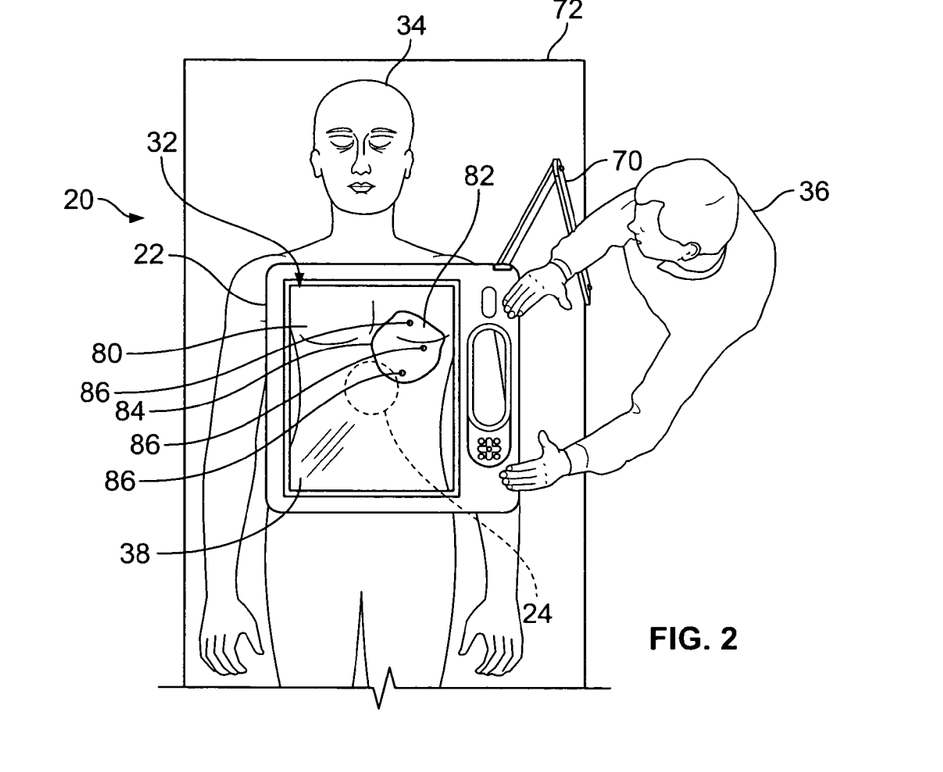
FIG. 2 shows a diagrammatic view of a display monitor of the navigation system of FIG. 1 positioned between the patient and an operator.
Figure 3:
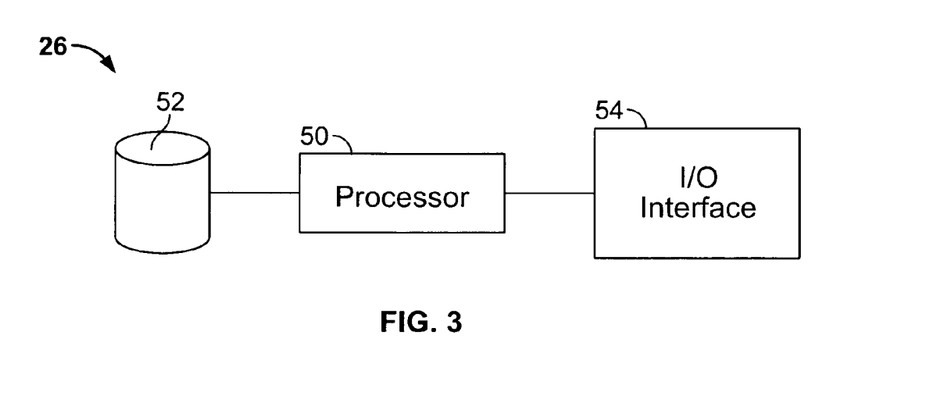
FIG. 3 is a block diagram of a CPU of the navigation system of FIG. 1.

Turning now to FIGS. 1-4, a navigation system 20 according to one aspect includes a display monitor 22, a camera 24, and a CPU 26 (see FIG. 3). In the present embodiment, the camera 24 is an optical camera that is able to detect the whole visible wavelength range and takes pictures and/or videos of a viewing area 28. The camera 24 is rigidly attached to a back side 30 of the display monitor 22 to form a monitor unit 32 so that the camera 24 can be directed at a body of a patient 34 or at least a part of the body of the patient while an operator 36 can view images displayed on a front side 38 of the monitor 22. The operator 36 may be a surgeon, a nurse, or any other observer or operating personnel. In the present embodiment, the camera 24 is centered in the back side 30 of the monitor 22 and, preferably, the display monitor 22 is aligned orthogonally with a focal axis of the camera so that, when the monitor unit 32 is positioned between the operator 36 and the patient 34, image data sets and visible images of the patient 34 can be displayed on the monitor 22 to give the impression to the operator 36 of having a direct view onto the patient 34 that eliminates any hand-eye coordination problems. In FIG. 1, a reference unit 40 is attached to the patient 34 within the viewing area 28. The camera 24 detects the reference unit 40 within an aperture angle 42 about the focal axis of the camera (generally coincident with the line indicating distance 44), wherein the aperture angle 42 and a distance 44 of the camera 24 from an object, such as the patient 32, defines the viewing area 28. The reference unit 40 may serve as a tracking device to compensate for movements of the patient with respect to the monitor unit 32 (according to one embodiment described with respect to FIGS. 12-16) and can be used to register the patient relative to the monitor unit 32, as will be described in more detail hereinafter. Further, the reference unit 40 may serve only as a registration device (such as shown in FIGS. 4-11) and there may be three or more such reference units located on the patient.

As seen in FIG. 3, an embodiment of the CPU 26 according to one possible aspect includes a processor 50, a memory or some other computer readable medium 52, and an input/output interface 54. The processor 50 is preferably an electronic digital computer commonly known or used in the art that implements software stored in the memory 52 to control the operation of the navigation system 20, wherein the software includes one or more routines that are implemented to perform various functions disclosed herein, such as obtaining and processing image data sets and visual images, automatically extracting usable data from the image data sets and visual images, tracking, and registering. In addition, the memory 52 can be configured to store other data, such as image data sets of a patient and surgical plan information. The input/output interface 54 allows the CPU 26 to interact with input and output devices, such as a flash memory drive, a CD/DVD drive, a keyboard, a mouse, a camera, a visual display, and the like. In the present embodiment, the CPU 26 is incorporated into the display monitor 22. However, in other embodiments, modifications to the CPU 26 can be made without departing from the spirit of the present disclosure. For example, the CPU 26 may include various other components and/or can be an external device coupled to the display monitor 22 and the camera 24 via a wired or wireless communication link, as would be apparent to one of ordinary skill in the art.

Figure 4:
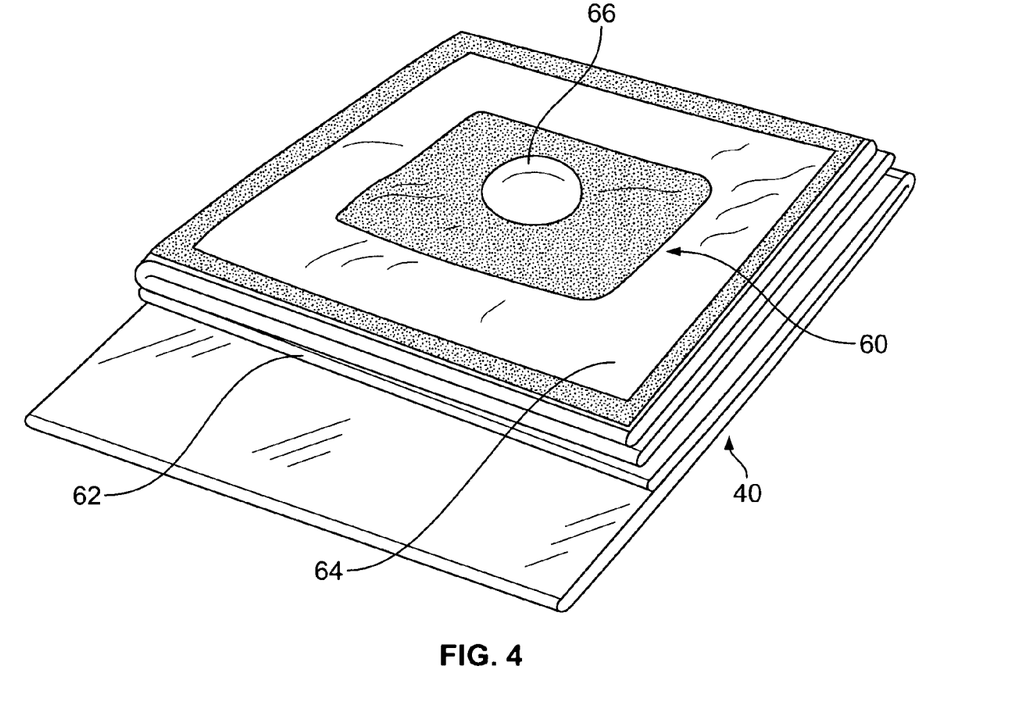
FIG. 4 is a perspective view of a reference unit usable with the navigation system of FIG. 1.

FIG. 4 illustrates an embodiment of the reference unit 40 that is an optical reference marker 60 detectable by the camera 24. The optical reference marker 60 is characterized by a generally planar, rectangular shaped body 62 with an optical pattern 64 of high optical contrast on the surface of the body 62. The optical pattern 64 is characterized by alternating angular light and dark contrast areas. However, in other embodiments, the optical pattern 64 can be modified to include curved lines, unique shapes, etc., as would be apparent to one of skill in the art. Further, the optical pattern 64 can be replaced by infrared characteristics detectable by an infrared camera. The infrared characteristics may be unique or uniform depending on the intended use. In the present embodiment, the reference unit 40 also includes a radiopaque reference marker 66 detectable in the image data set and disposed in the center of the optical pattern 64. The radiopaque reference marker 66 is a ball-shaped marker and is made of a substance, such as metal, in order to be detectable in CT, MR, PET, X-ray, and other similar imaging modality data sets. However, depending on the pre-operative imaging system, the reference marker 64 can be made of any other material suitable for being detected by various imaging systems. Further, the radiopaque reference marker 66 can be any shape that would be apparent to one skilled in the art. Referring again to the present embodiment, the optical reference marker 60 delineates a generally rectangular shape, the center of which corresponds to the center of the radiopaque reference marker 66. The optical reference marker 60 is recognized by the navigation system 20 by using, for example, software that implements standard pattern matching algorithms such as "iterative closest points," and serves as a registration pattern to correlate the position of the patient 34 relative to the camera 24. In some embodiments, the optical reference marker 60 is used for tracking movement of the patient relative to the camera 24. One or more reference units 40 can be used to correlate the position of the patient 34 relative to the camera 24, as would be apparent to one of skill in the art.

Referring to FIG. 2, the monitor unit 32 is positioned between the operator 36 and the patient 34 with a fastening mechanism that allows the monitor 22 to be fixed in a certain position with respect to the patient 34 or moved out of the line-of-sight between the operator 36 and the patient 34, if desired. In one embodiment, the fastening mechanism includes a movable arm 70 connected between an operating room table 72 and the monitor 22. Other modifications to the fastening mechanism can be made, as would be apparent to one of ordinary skill, for example, the movable arm 70 can be connected to a cart or some other support structure. In another embodiment, the fastening mechanism can be omitted and the monitor unit 32 can be a hand-held device that is wireless and battery-powered (see, e.g., FIG. 11).

In FIG. 2, the monitor unit 32 is positioned with the camera 24 directed at a torso of the patient 34 and the front side 38 of the monitor 22 generally facing the operator 36. The camera 24 obtains a visible image 80 of the outer surface of the patient 34, i.e., an actual view of the patient position with respect to the camera 24, which is displayed on the display monitor 22. Additionally, an image data set 82 that corresponds to virtual patient data is acquired and transferred to the monitor 22. For example, the image data set 82 can be acquired during a pre-operative imaging step and loaded to the CPU 26 via an appropriate data transfer interface. Such image data set 82 can include internal structure data 84 that is not readily visible through the skin or outer surface of the patient to the camera 24, for example, an image of an organ, boney structure, tumor, and the like acquired with one or more imaging modalities, such as 2-dimensional X-ray, CT, MR, and/or PET. In one embodiment, the image data set 82 is displayed on the display monitor 22 superimposed on the visible image 80 of the patient 34. In another embodiment, the visible image 80 and the image data set 82 can be displayed next to each other or alternately switched.

In order to accurately display the image data set 82 superimposed on the visible image 80 and, more preferably, to display the image data set 82 in the same position and orientation as the body of the patient 34 as viewed by the camera 24, a manual or automatic registration procedure is performed. In the present embodiment, three predetermined points 86 of the image data set 82 (see FIG. 2) are registered to corresponding points 88 on the body of the patient 34 (see FIG. 1). The image data set 82 may alternatively be registered with the patient 34 by correlating a predetermined surface of the image data set 82 with a corresponding surface on the body of the patient 34.

In one embodiment, the manual registration of the position of the patient 34 with respect to the image data set 82 is performed by a digitization process using a pointing device (not shown) that has known geometry and is equipped with one or more reference units, such as the reference unit 40' (according to FIGS. 12-16), or other types of known reference units. Depending on the needed accuracy, palpated points on the skin or rigid anatomical structures/landmarks can be used as digitized points on the patient 34. The digitized points 88 on the patient 34 are matched with corresponding pre-defined points 86 of the image data set 82 to register the patient position with the image data set 82 using methods and techniques that would be apparent to one of ordinary skill in the art.

When the registration procedure is finished, the navigation system 20 knows the transformation between the patient 34 and the actual position of the monitor unit 32. Such known transformation allows the camera 24 to serve as an integrated tracking system and, since the monitor 22 is rigidly fixed to the camera 24, spatial localization of the monitor 22 is not needed.

After registration, the image data set 82 is processed and displayed with an angle of view and aperture in accordance with and corresponding to the actual position of the patient 34 relative to the monitor unit 32. When the monitor unit 32 is positioned between the operator 36 and the patient 34, the operator 36 gets the impression of looking through the monitor 22 and seeing virtual internal structures 84 from the image data set 82. In one embodiment, the image data set 82 can be revised by the operator 36 to include additional information, for example, by selecting different internal structures 84, changing the color/contrast of internal structures 84, defining trajectories of surgical tools for a procedure, incision locations, and the like, wherein the revised image data set 82 can be displayed on the monitor 22.

During a surgical procedure, for example, one or more reference units 40 attached to the patient 34 are continuously tracked by the camera 24. If any movement takes place, for example, movement of the patient 34 or movement of the monitor unit 32, the navigation system 20 includes appropriate software and/or hardware capable of automatically extracting the movement from the video images in a manner known to one skilled in the art and of compensating for such movement so that the image data set 82 is continuously adapted to the position and orientation of the patient 34 with respect to the angle of view and the aperture angle 42 of the camera 24. Examples of such automatic image data extraction technology include computer software that implements "surface rendering" and "threshold based volume segmentation," and other automatic image data extraction technology may also or alternatively be used. Consequently, when the monitor unit 32 is moved around the patient 22 or vice versa, the operator 36 can see the internal structures 84 from the image data set 82 and the additional information, such as cut locations, tool trajectory paths, and/or other information, from different directions and angles corresponding to the view of the camera 24.

As described above, the reference units 40 can be used for tracking purposes. However, in other embodiments, the reference units 40 can also be used for registration purposes. More specifically, an automatic registration procedure can be performed with the reference units 40, as described hereinafter with reference to FIGS. 5-11.

Figure 5:
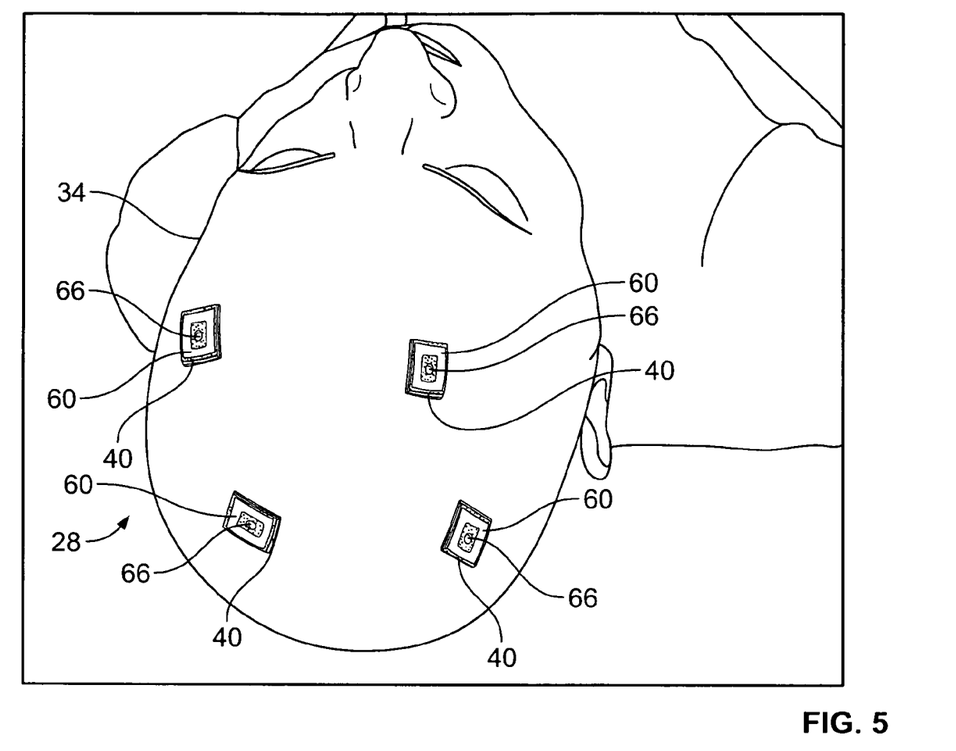
FIG. 5 shows a number of reference units according to FIG. 4 attached to a patient.
Figure 6:
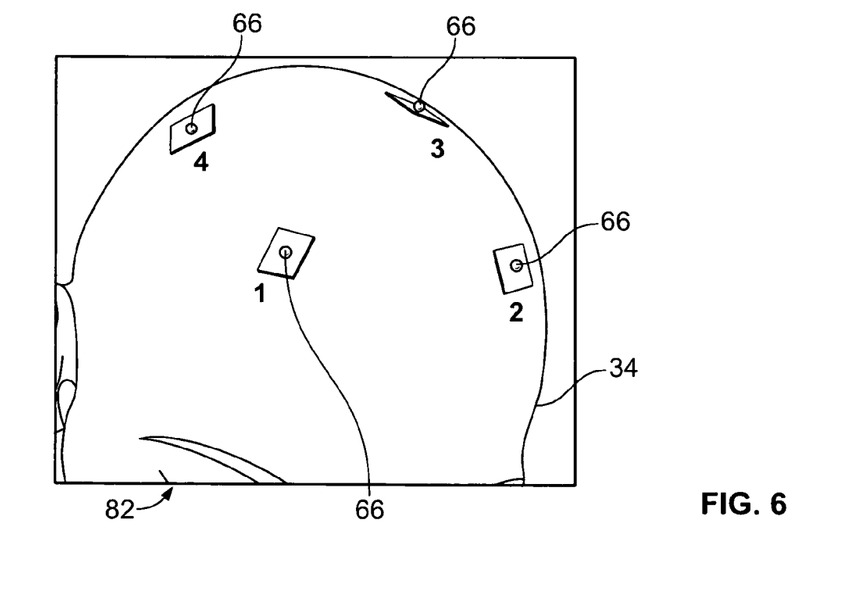
FIG. 6 illustrates an image data set of a patient that includes visible portions of the reference units of FIG. 5.
Figure 7:
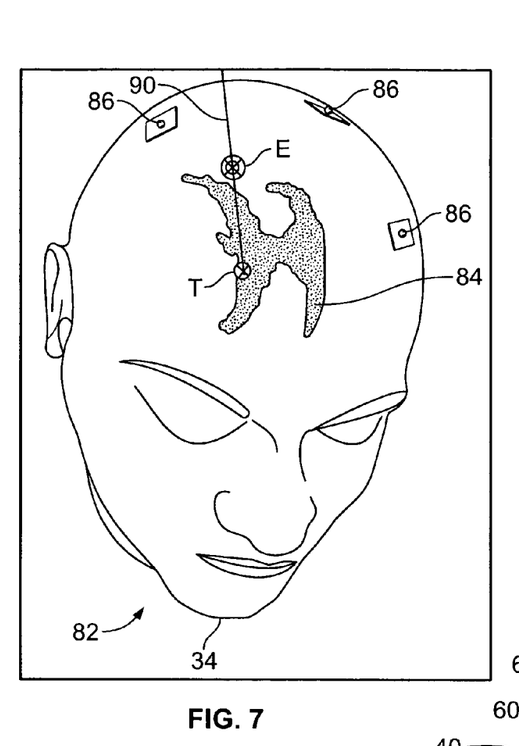
FIG. 7 illustrates an image data set of a patient that includes visible portions of the reference units of FIG. 5, an internal structure of the patient, and additional virtual information.

FIG. 5 shows a body part of interest, such as a head of the patient 34, which is provided with four reference units 40 before the acquisition of the image data set 82. The reference units 40 are within the viewing area 28 of the camera 24. Generally, three reference units 40 are sufficient for registration purposes to reveal information about the position and orientation of the image data set 82 with respect to the camera 24. However, in other embodiments, additional reference units 40 can be used, which will result in an increased accuracy, field of view, and robustness of the navigation system 20. FIG. 6 illustrates an image data set 82 acquired with CT, wherein only the radiopaque reference markers 66 of the reference units 40 are visible. The centers of the reference units 40 are automatically found by a software algorithm that may be a part of the software stored in the memory 52 of the CPU 26. In the present example, the centers of the radiopaque reference markers 66 form the predetermined points 86 in the image data set 82. One or more internal structures 84 can be selected from the image data set 82, as can be seen in FIG. 7, and the operator 36 can also define additional information with respect to the image data set 82, such as, a planned trajectory 90 for a surgical instrument with an entrance point E and a target point T, an operation plan, and/or other similar virtual surgical plan information. Surgical instruments may also be equipped with appropriate reference units 40, representations of which can be superimposed on the image data set 82 along with the internal structure 84 and additional information.

Figure 8:
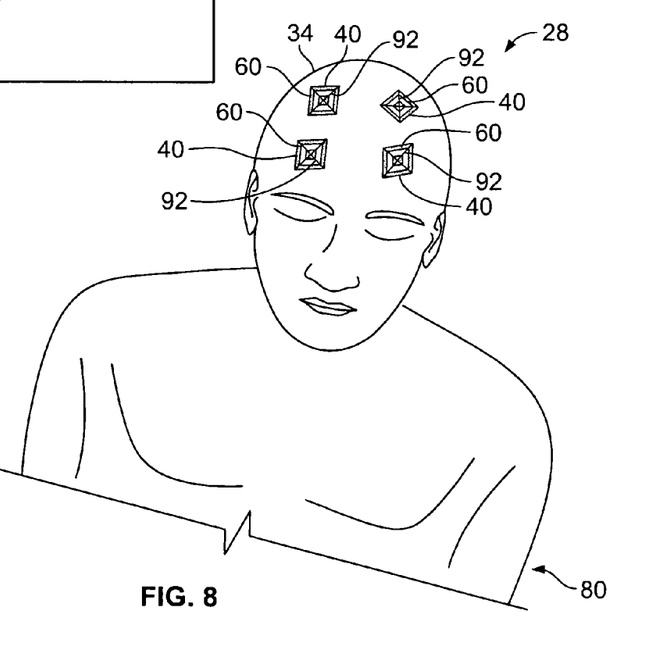
FIG. 8 is a diagrammatic view of a visible image of a patient that includes portions of the reference units of FIG. 5.
Figure 9:
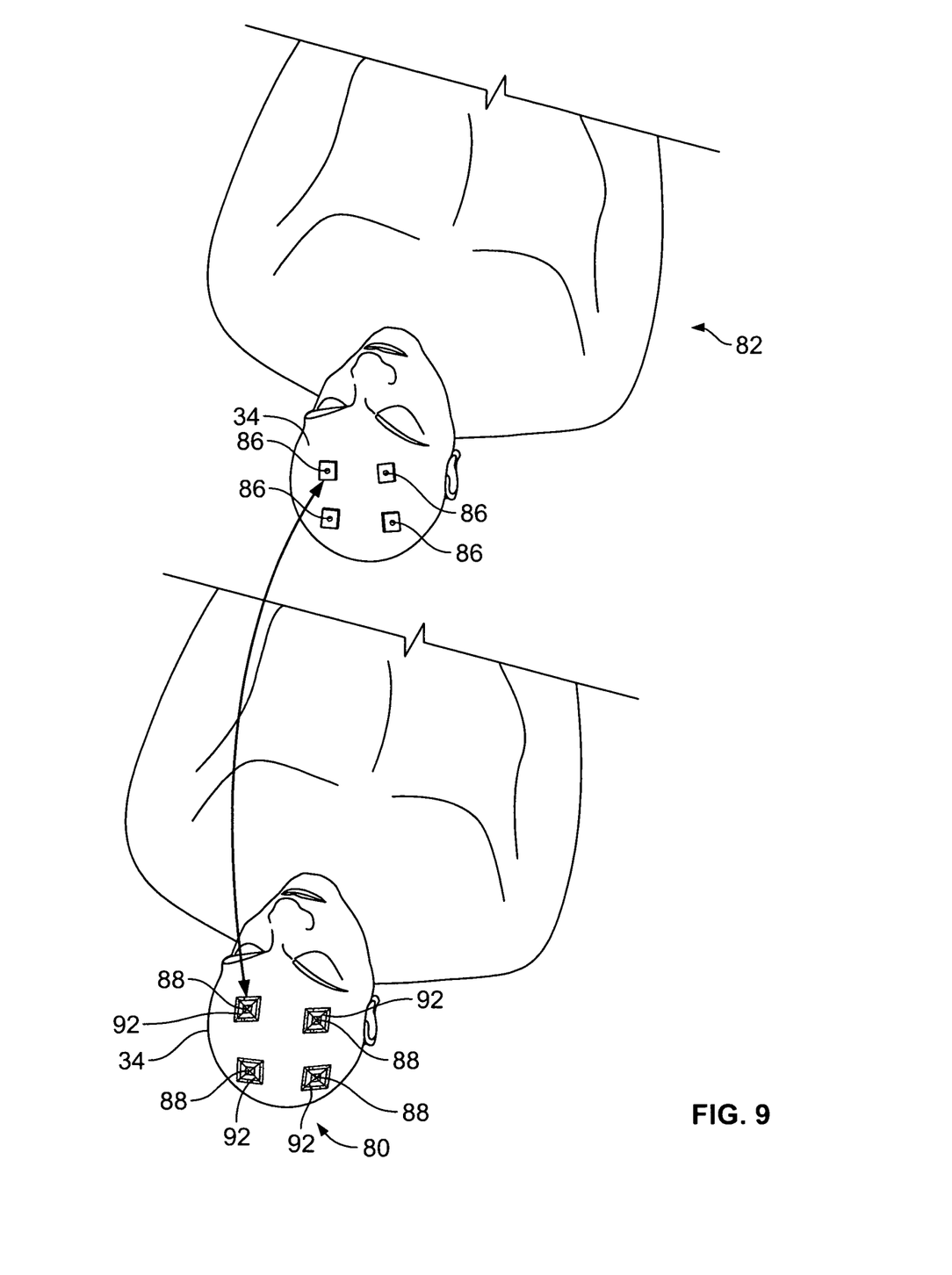
FIG. 9 is a diagrammatic view of a procedure to register a position of a patient from a visible image with an image data set of the patient.

After coordinates of the four predetermined points 86 of the image data set 82 are known, the spatial positions of the corresponding points 88 on the patient 34 are determined. In one embodiment, due to the optical pattern 64 of the reference units 40, the navigation system 20 can automatically detect and determine the centers thereof shown as midpoints of crosses 92 defined by the corners of the reference units 40, as can be seen in FIG. 8. In a further step shown in FIG. 9, registration is accomplished by the CPU 26 by correlating each predetermined point 86 of the image data set 82 with the corresponding point 88 on the visible image 80 of the patient 34 while being viewed by the navigation system 20, such as during a surgical operation. The registration process may be performed on the CPU using a software algorithm known or readily understood in the art, such as the iterative closest point matching algorithm, or other known methods.

Figure 10:
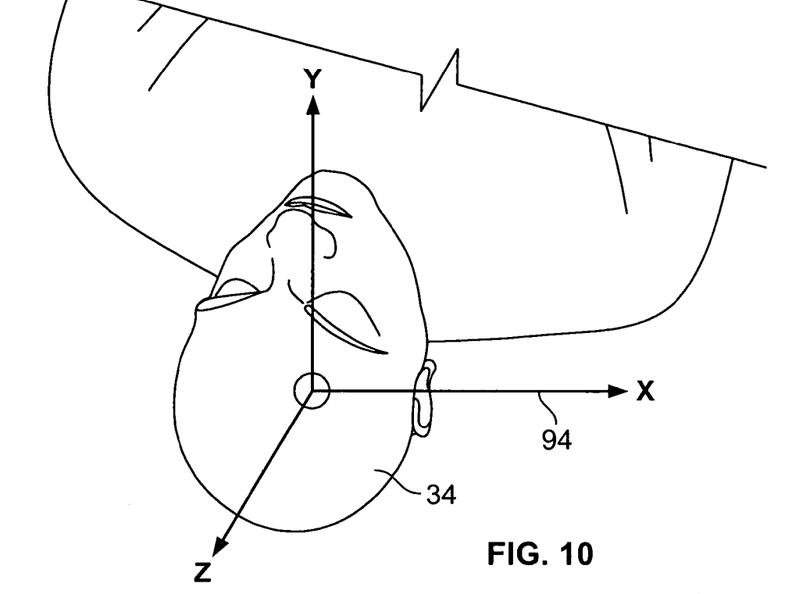
FIG. 10 is a diagrammatic view that shows a patient with respect to an image data set coordinate system.
Figure 11:
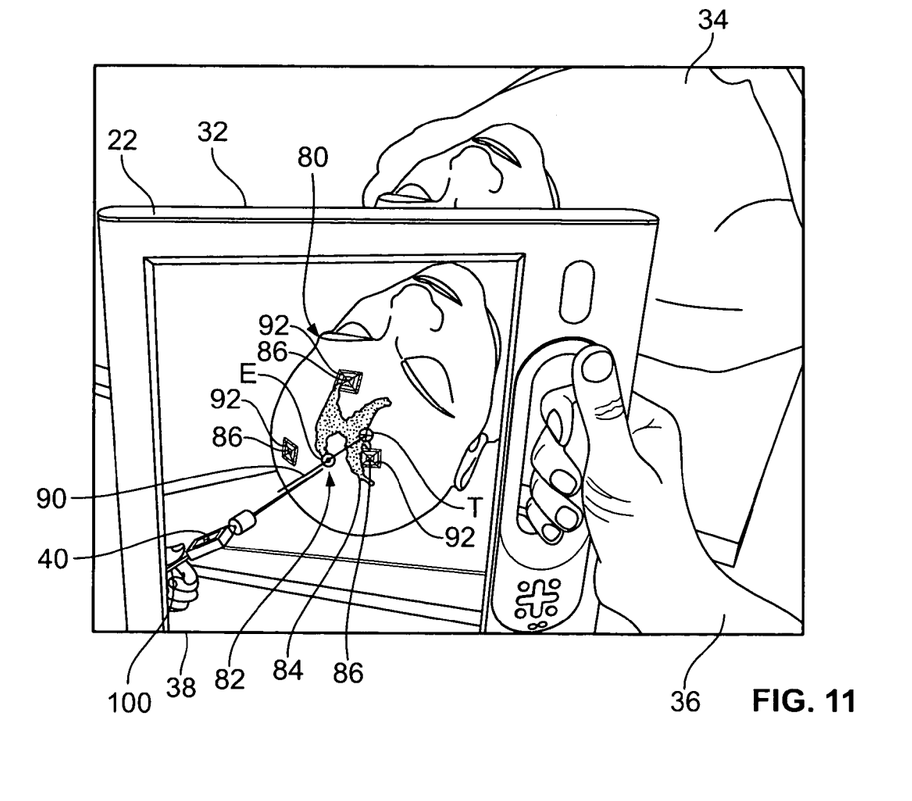
FIG. 11 shows a display monitor of the navigation system of FIG. 1 positioned between the patient and an operator, wherein the display monitor displays a visual image of the patient superimposed with data from an image data set.

After registration, an image data coordinate system 94 is established, wherein the position and orientation of the image data set 82 with respect to the patient 34 is known (see FIG. 10). Using the established image data coordinate system 94, the internal structure 84 and the additional information can be displayed on the monitor 22 (see FIG. 11) superimposed with or on the visible image 80 from the camera 24 and aligned with the viewing area 28 of the patient 34 through the camera. In this embodiment, a surgical instrument 100 with known geometry is also equipped with one or more reference units 40 (and/or 40' and/or 40" described below) and tracked by the navigation system 20. The monitor 22 of FIG. 11 displays features of the surgical instrument 100. As seen in FIG. 11, the surgical instrument 100 can be aligned with the trajectory 90 from the image data set 82 to aid in the execution of a surgical procedure. Such alignment in one embodiment may be achieved solely by visible alignment of the visible image of the instrument with the virtual planning information, such as the trajectory 90. In another embodiment, the alignment may be enhanced or replaced with additional tracking and guidance assistance through the CPU 26 or other computer to show a virtual image or graphic representation of the instrument, such as, portions of the instrument that are not visible to the camera 24 below the outer surface of the patient.

In the automatic registration procedure of FIGS. 4-11, it is not necessary that the optical reference markers 60 of the reference units 40 differ from each other. However, in some embodiments, the optical reference markers 60 of the reference units 40 may differ from each other. For example, in FIG. 12 another reference unit 40' is shown that differs from the reference unit 40 of FIG. 4 by the addition of a unique distinguishing feature 96, such as a number or the like, to the body 62 of the reference unit 40'. The optical pattern 64 shown in FIG. 12 includes the sign "I" in a corner thereof. Otherwise, the reference units 40 and 40' are substantially similar.

Figures 12, 13, 14:
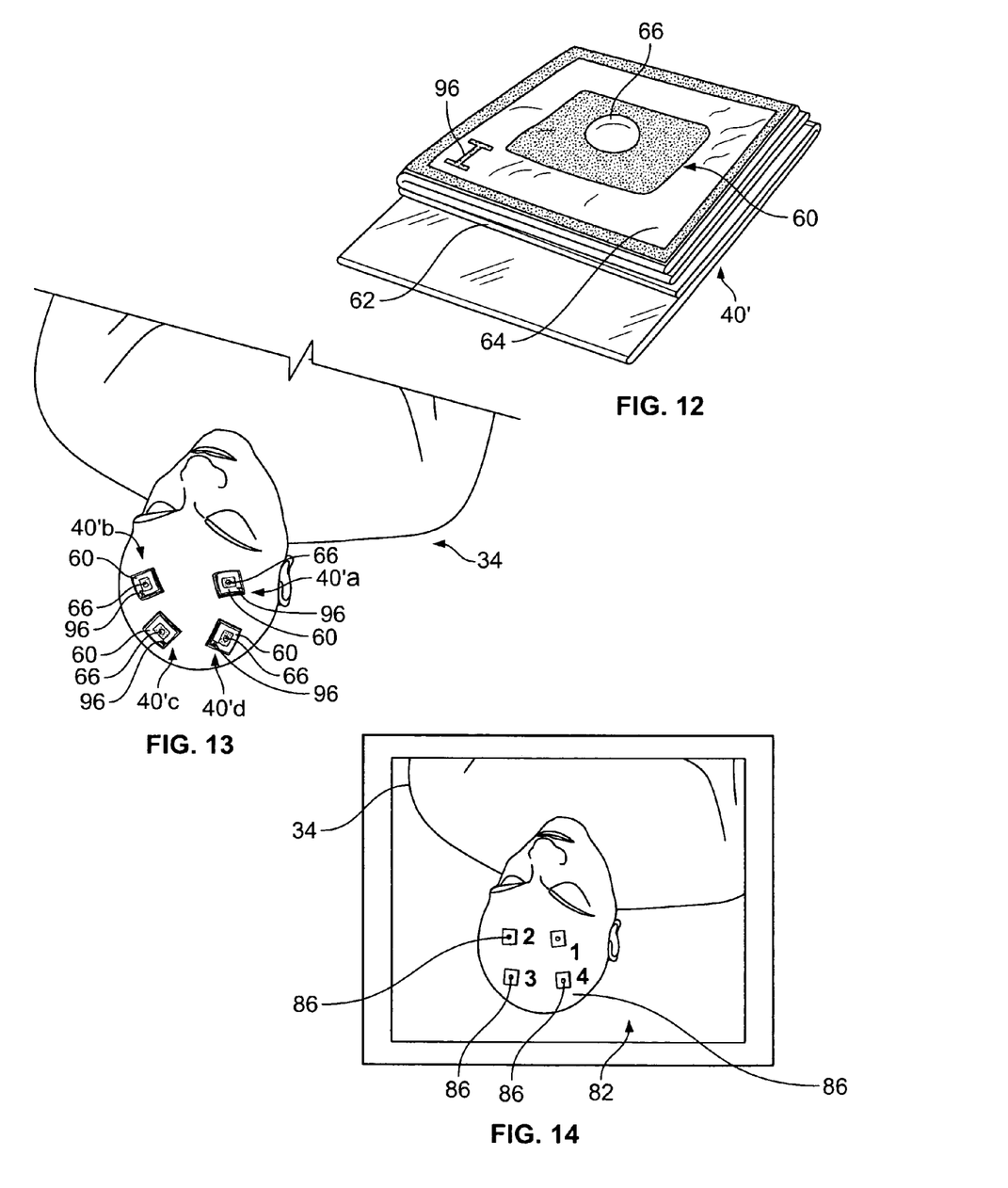
FIG. 12 is a perspective view of another reference unit usable with the navigation system of FIG. 1.
FIG. 13 is a diagrammatic view of a plurality of reference units according to FIG. 12 attached to a patient.
FIG. 14 is a diagrammatic view of an image data set of a patient that includes a unique image signal based on visible portions of the reference units of FIG. 13.
Figure 15:
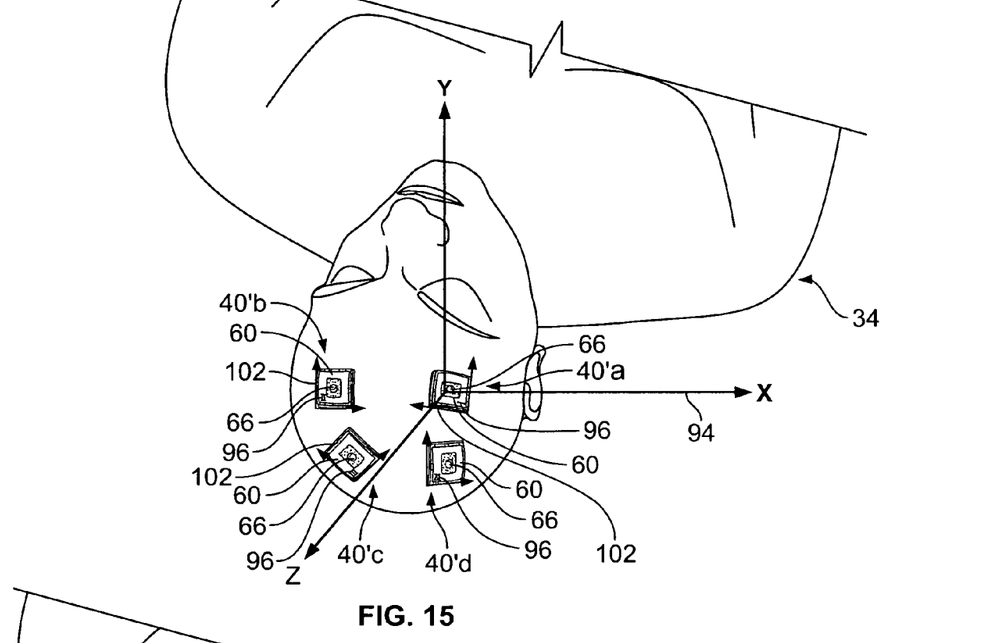
FIG. 15 is a diagrammatic view that shows the orientation of the reference units of FIG. 13 with respect to an image coordinate system.
Figure 16:
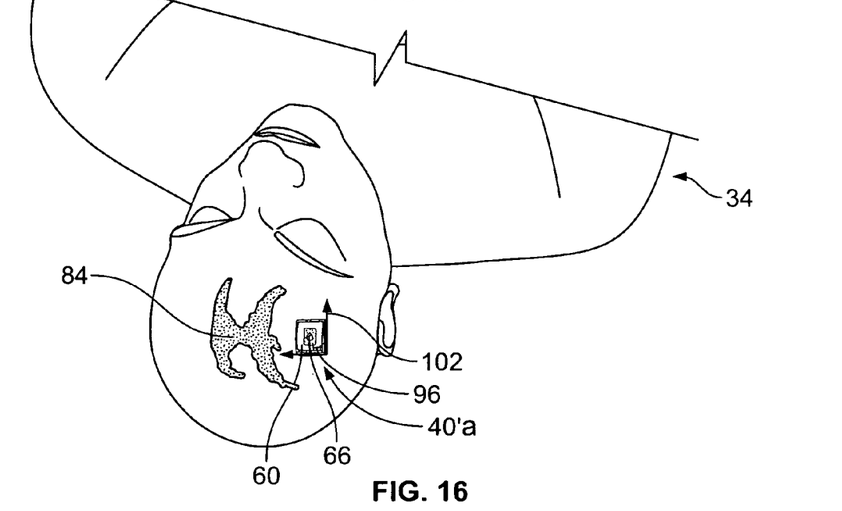
FIG. 16 is a diagrammatic view that shows an internal structure superimposed on the body of a patient and the orientation of a reference unit of FIG. 15.

In the embodiment of FIGS. 12-16, the acquisition of the visible image 80 and the image data set 82 and the registration procedure are performed in the same way as described above. The first step comprises affixing the reference units 40' to the body of the patient 34 prior to the acquisition of the image data set 82. As shown in FIG. 13, four unique reference units 40'a, 40'b, 40'c, and 40'd are fixed to the head of the patient 34, such as with adhesive. The optical patterns 64 of the reference units 40'a-40'd comprise distinguishing features 96 in the form of different numbers "I, II, III, and IV" located at the corners of the reference units 40'a-40'd, respectively. After acquisition of the image data set 82 is accomplished, the coordinates of the radiopaque reference markers 66 are determined to establish the predetermined points 86 of the image data set 82 (see FIG. 14). Then, the camera 24 acquires a visual image 80 of the patient 34 and the centers of the optical patterns 64 are determined within the visual image 80. The centers of the radiopaque reference markers 66 from the image data set 82 and the centers of the optical patterns 64 from the visual image 80 are correlated point-by-point in order to register the orientation of the patient 34 with respect to the image data set 82. Since the four reference units 40'a-40'd differ from each other, the navigation system 20 can register a coordinate system 102 of each reference unit 40'a-40'd with respect to a single coordinate system 94 of the image data set 82 (see FIG. 15). The distinguishing feature 96 provides one unique known orientation of the optical pattern 64 with respect to a three-dimensional x-y-z coordinate system 102 of each individual reference unit 40'a, 40'b, 40'c, and 40'd, which allows the location and orientation of the coordinate system 102 to be identifiable from any viewpoint from which the entire optical pattern 64 is visible. Also, the position and orientation of each unique reference unit 40'a-40'd is known with respect to the orientation of the patient 34. Therefore, the navigation system 20 can recognize each reference unit 40'a-40'd separately by means of appropriate image data extraction software implemented by the CPU 50 and can identify uniquely the location, orientation, and scale of each reference unit 40'a-40'd with respect to the coordinate system of the camera 24. As a result, after registration, a single reference unit (for example, reference unit 40'a) is sufficient for navigation purposes and for augmentation of the visual image 80 with internal structures 84 and information from the image data set 82 (see FIGS. 15 and 16).

After the registration procedure is complete, the number of reference units 40' can be reduced and a single reference unit 40' used to track the patient 34. Alternatively, the number of reference units 40' can be increased in order to enlarge the visibility range of the navigation system 20 and/or to increase navigational stability if one or more reference units 40' are covered by the operator 36 and are no longer detectable by the camera 24. The added reference units 40' may omit the reference markers 64. Also, in the case of manual registration described above, the at least one reference unit 40 does not need to comprise the radiopaque reference marker 66.

Figure 17:
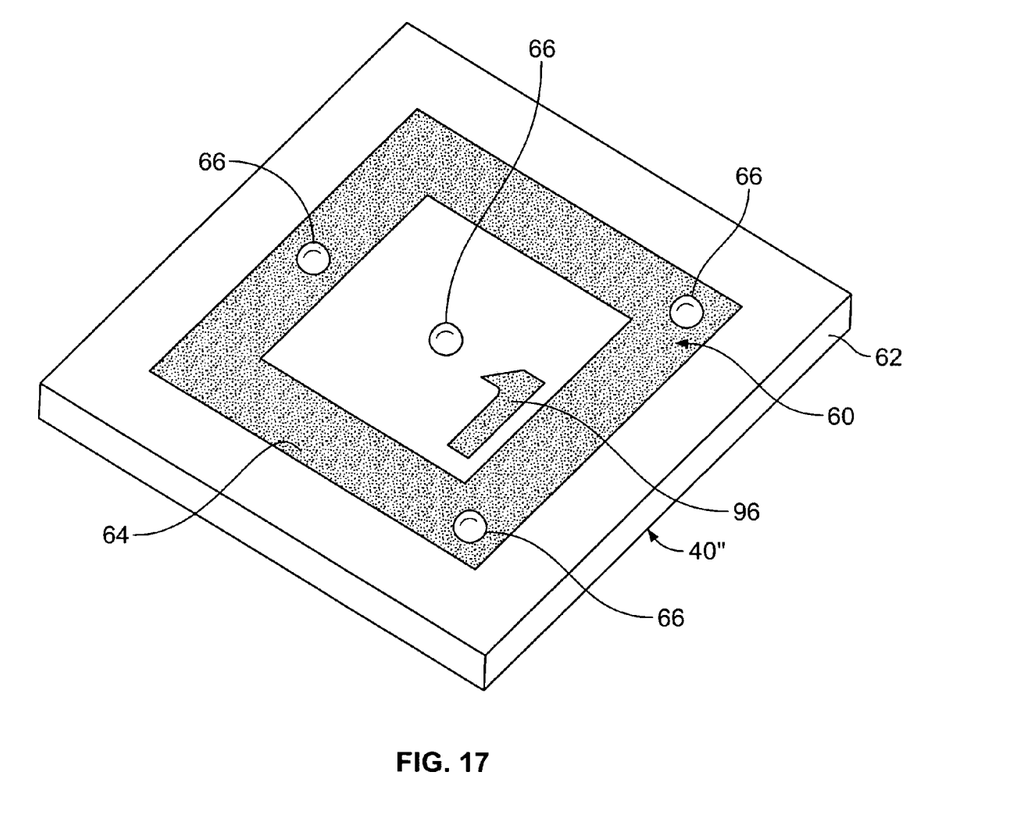
FIG. 17 is a perspective view of yet another reference unit usable with the navigation system of FIG. 1.

Referring now to FIG. 17, another reference unit 40" is shown that has one or more features that create a unique image signal in the image data set and a unique representation in the visual optical image. Each of the unique image signal and unique representation includes identifiable reference locations, points, and/or surfaces, which allows the navigation system to both register a pre-operative image data set with an intra-operative image of the patient and to continually track the location and orientation of the patient using a single reference unit 40". The reference unit 40" is similar to the reference unit 40' in that the reference unit 40" also includes a unique distinguishing feature 96, for example the number "1" disposed near a corner of the rectangular optical pattern 64, although the unique distinguishing feature 96 can include other combinations of numbers, letters, markings, patterns, and the like, as would be apparent to one of ordinary skill in the art. Further, the reference unit 40" includes a plurality of radiopaque reference markers 66, such as metal balls. In one example, the reference unit 40" includes four radiopaque reference markers 66, preferably including one central radiopaque reference marker located in the center of the optical pattern 64 and three peripheral radiopaque reference markers disposed in a generally triangular pattern around the central radiopaque reference marker. The radiopaque reference markers are non-linearly aligned, preferably in an orientationally unique pattern defining a single unique coordinate axis. Three radiopaque reference markers 66 or more than four radiopaque reference markers 66 may also be used and obtain the same functionality. Preferably, the combination of the optical pattern 64 and the distinguishing feature 96 produces a uniquely identifiable visual pattern that creates a unique representation from each and every possible angle of view of the camera 24, i.e., the visual pattern identifies or defines a single unique three-dimensional coordinate system that can be determined from any viewing angle, whereby the location and orientation of the reference unit 40" can be positively and uniquely identified from any angle of view of the camera 24 without requiring a second and/or third marker 40" in the field of view of the camera 24. The radiopaque reference markers 66 are also arranged such that a unique visual pattern of the radiopaque reference markers 66 is created from every practicable viewing angle, and the radiopaque reference markers 66 are located in known uniquely identifiable positions with respect to the optical pattern 64, whereby the image data set 82 can be registered to the visible image 80 of the patient using a single reference unit 40". In addition, the entire image data set 82 can be continually tracked using only a single reference unit 40" because of the uniquely identifiable visual pattern created by the optical pattern 64 with the distinguishing feature 96. Additional reference units 40" may be used to increase the robustness of the navigation system 20 with respect to accuracy, field of view, and/or other redundant parameters, but such additional markers 40" may not be necessary for the proper functioning of the navigation system 20. A similar registration and tracking procedure as described with respect to the reference unit 40' in FIGS. 12-16 can be followed using the reference units 40" of FIG. 17, except that both the registration operation and the tracking operation can be accomplished with a single one of the reference units 40". When the registration procedure is finished, the navigation system 20 knows the coordinate transformation, rotation, and scale between the patient 34 and the actual position of the monitor unit 32. Such known transformation allows the camera 24 to serve as an integrated tracking system and, since the monitor 22 is rigidly fixed to the camera 24, spatial localization of the monitor 22 is not needed. Adhesive may be disposed on the back side of the body 62 of the reference marker 40" (and similarly with reference markers 40 and 40') opposite the side carrying the optical pattern 64 in order to facilitate affixing the reference marker to an outer surface of the body, such as the skin of the patient 34.

INDUSTRIAL APPLICABILITY

Embodiments of the present disclosure can have many useful applications. Some anticipated applications include use in medical or surgical procedures such as general surgery, orthopedic surgery, cranial surgery, and diagnostic interventions, such as biopsies. Further, embodiments of the present disclosure may also be useful for any kind of minimally invasive procedure, such as in the abdominal region, any kind of endoscopic procedure, incision planning, locating the rough global position of an endoscope or any other surgical instrument, and other surgical procedures where visualization of an interior of a patient body during the procedure is helpful to the operator. Other embodiments and uses of the present disclosure outside of a medical context are also anticipated and are within the scope of the present disclosure, for example, for remote operation of maintenance equipment within an enclosed environment, such as a boiler or piping system, by way of example only.

In some embodiments, the disclosed system and method may provide for improved spatial orientation and targeting of anatomical structures and reduced radiation exposure to the patient and/or operator(s). Further, the system in some embodiments may ease the challenge of monitoring and combining virtual and real surgical environments for the surgeon, solve hand-eye-coordination issues, provide for automatic registration of pre-operative patient information with intra-operative patient information, and/or reduce the complexity and cost of equipment in the operating room as compared to existing navigation systems.

Numerous modifications to the present invention and uses thereof will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications that come within the scope of the appended claims are reserved.

We claim:

1. A system for visualizing an interior of a body from an exterior position, comprising:
    a navigation system having a monitor and a camera, wherein the camera is rigidly fixed to the monitor and serves as a global reference system, wherein the monitor is movably positionable between an operator and the body;
    an optical reference unit adapted to be attached to the body for tracking movements of the body;
    an electronic processing device in communication with the navigation system; and
    an image data set comprising features of the interior of the body, the image data set being accessible to the processing device;
    wherein the processing device receives an optical image of an exterior surface of the body obtained with the camera, registers the image data set with respect to the global reference system of the camera by matching a spatial position of the optical reference unit in the image data set with a spatial position of the optical reference unit in the optical image without tracking either the monitor, or the camera, and causes the monitor to display the image data set superimposed and in registration with the optical image in a position and orientation that represents an angle of viewing and an aperture angle of the camera relative to the body.

2. The system of claim 1, wherein the monitor is aligned with a focal axis of the camera.

3. The system of claim 2, wherein the monitor is on a first side of the navigation system and the monitor comprises a back side, the camera is rigidly mounted to the back side of the monitor.

4. The system of claim 3, further comprising a movable arm, wherein the navigation system is carried by the movable arm, and wherein the movable arm is connected to a support structure.

5. The system of claim 1, further comprising surgical plan information, wherein the processing device continually tracks movement of the body relative to the camera, and wherein the processing device causes the monitor to display the surgical plan information superimposed with the optical image in a position and orientation in registration with the optical image.

6. The system of claim 5, wherein the surgical plan information includes at least one of a target location inside the body and a trajectory path for a tool and an incision location on the body.

7. The system of claim 1, wherein the optical reference unit includes an optical pattern of alternating light and dark contrast areas that are detectable by the processing device in the optical image and a radiopaque marker that is visible in the image data set, wherein the radiopaque marker is in an identifiable and known location with respect to the optical pattern.

8. The system of claim 7, wherein the optical pattern includes a distinguishing feature, wherein the distinguishing feature causes the optical pattern to be unique from each possible viewing angle.

9. The system of claim 8, wherein the optical reference unit comprises at least three radiopaque markers.

10. The system of claim 1, wherein the optical reference unit includes an optical pattern that provides functionality as a tracking device and a sufficient number of markers that are detectable in the image data set to provide functionality as a registration device, wherein the reference unit enables automatic registration of the image data set to the optical image by the processing device.

11. A method of visualizing an interior of a body from an exterior viewing position, the method comprising the steps of:
    obtaining an internal image data set of an internal portion of the body, wherein the internal image data set includes a reference location on an exterior surface of the body;
    accessing the internal image data set with a navigation system comprising a visual display screen, a camera rigidly fixed to the visual display screen in alignment with the display screen, and a digital electronic processing unit in data communication with the camera and the display screen, wherein the camera serves as a global reference system and the visual display screen is movably positionable between an operator and the body;
    obtaining a visual image of an exterior of the body with the camera, wherein the reference location is visible in the visual image and oriented to the global reference system;
    identifying the reference location in the visual image;
    registering with the digital electronic processing unit the internal image data set to the visual image in relation to the global reference system of the camera by matching a spatial position of the reference location in the internal image data set with a spatial position of the reference location in the visual image without tracking either the monitor or the camera;
    displaying the internal image data set superimposed and in registration with the visual image on the visual display screen in a position and orientation that represents an angle of view and an aperture angle of the camera and the visual display screen relative to the body;
    tracking movements of the body with respect to the camera using the reference location in the visual image; and
    updating the display of the internal image data set with the digital electronic processing unit to correspond with the position of the body with respect to the camera based on the tracked movements of the body.

12. The method of claim 11, wherein the step of registering comprises at least one of the step of performing a point by point correlation of one or more reference points between the internal image data set and the visual image, the step of performing a surface to surface correlation between the internal image data set and the visual image, and the step of digitizing points on the body with a pointing device in the visual image and correlating the digitized points with one or more corresponding reference locations in the internal image data set.

13. The method of claim 11, wherein the step of obtaining an image data set comprises the step of attaching a reference unit comprising the reference location to the body, wherein the reference unit comprises an optical pattern and at least one radiopaque marker, wherein the radiopaque marker is visible in the internal image data set and the optical pattern is visible in the visual image, wherein the radiopaque marker is in a known unique relation to the optical pattern, and wherein the step of registering comprises correlating positions of the radiopaque marker in the internal image data set with the optical pattern in the visual image.

14. The method of claim 13, wherein the step of updating comprises the steps of tracking movements of the reference unit relative to the camera using at most one reference unit.

15. The method of claim 11, further comprising the step of displaying virtual information relevant to a planned location of interest in a surgical procedure on the internal image data set along with the image data set on the visual display.

16. The method of claim 15, wherein the step of displaying virtual information further comprises displaying a planned trajectory of an instrument to be inserted into the body in registration with the internal image data set and the visual image.

17. The method of claim 11, wherein the image data set comprises image data regarding one or more internal structures inside the body, and wherein the step of displaying the internal image data set includes the step of selecting one or more of the internal structures to display.

18. The method of claim 15, further comprising the step of tracking an instrument in a field of view of the camera with known geometry that is equipped with at least a second reference unit.

19. The method of claim 18, further comprising the step of superimposing a representation of a feature of the instrument on the monitor in registration with the internal image data and the virtual information.

20. The method of claim 11, wherein the step of registering the internal image data set to the visual image further comprises the steps of:
affixing at least one reference unit to the exterior surface of the body at the reference location, wherein the reference unit has one or more features that create a unique image signal in the image data set and a unique representation in the visual image;
acquiring the image data set that includes the unique image signal of the reference unit;
identifying the position of the reference unit with respect to a coordinate system of the internal image data set;
acquiring the visual image of the exterior surface of the body that includes the unique representation of the reference unit;
identifying the position of the reference unit in the visual image; and
matching the spatial position of the reference unit in the internal image data set with the spatial position of the reference unit in the visual image to automatically register the internal image data set with the visual image of the body.

21. The method of claim 20, further comprising the step of affixing at least three of the reference units to the body, determining the orientation and size of the reference units based on a different unique optical pattern disposed on each of the reference units, and registering the orientation of the reference units with a coordinate system of the body.

22. The method of claim 20, further comprising the step of utilizing a navigation system that includes a monitor, a camera fixed to the monitor, and an electronic processor, wherein the navigation system performs the step of matching the spatial position.

23. The method of claim 20, wherein the step of identifying the position of the reference unit in the visual image includes the step of identifying the center of the reference unit with the electronic processor, and the step of matching includes the step of matching the spatial position of the reference unit in the internal image data set with the center of the reference unit in the visual image with the electronic processor.

24. The method of claim 20, wherein the features of the reference unit include one or more reference markers that are detectable in the image data set to create the unique image signal in the image data set and an optical pattern of alternating light and dark contrast areas that are detectable in the visual image to create the unique representation.

25. The method of claim 24, wherein the reference unit includes three or more radiopaque reference markers, and wherein a single reference unit is affixed to the body to register the image data set with the visual image and to track movement of the body.

* * * * *